United States Patent
Choi et al.

(10) Patent No.: US 8,779,192 B2
(45) Date of Patent: Jul. 15, 2014

(54) PROCESS OF PREPARING AN ALKYLAMINE DERIVATIVE

(75) Inventors: Yoon-Hwan Choi, Suwon-si (KR); Won-Tae Chang, Yongin-si (KR)

(73) Assignee: Kolon Life Science, Inc., Kwacheon ( * ) Notice: Subject to any disclaimer, the term of this patent is extended or adjusted under 35 U.S.C. 154(b) by 13 days.

(21) Appl. No.: 13/318,268

(22) PCT Filed: May 14, 2010

(86) PCT No.: PCT/KR2010/003057
§ 371 (c)(1),
(2), (4) Date: Oct. 31, 2011

(87) PCT Pub. No.: WO2010/131921
PCT Pub. Date: Nov. 18, 2010

(65) Prior Publication Data
US 2012/0046494 A1   Feb. 23, 2012

Related U.S. Application Data

(60) Provisional application No. 61/178,117, filed on May 14, 2009.

(51) Int. Cl.
*C07C 229/00* (2006.01)
(52) U.S. Cl.
USPC ......................................................... 562/574

(58) Field of Classification Search
USPC ........................................................ 562/574
See application file for complete search history.

(56) References Cited

U.S. PATENT DOCUMENTS 7,126,025 B2 * 10/2006 Considine et al. ............ 562/868

FOREIGN PATENT DOCUMENTS

| | | |
|---|---|---|
| JP | 59192095 A | 10/1984 |
| JP | 2004509097 A | 3/2004 |
| WO | 2004/066919 A2 | 8/2004 |
| WO | 2006/127203 A2 | 11/2006 |
| WO | 2009/033581 A1 | 3/2009 |

OTHER PUBLICATIONS

F. A. Carey, Organic Chemistry, 5th edition, Chapter 20: Hydrolysis of Esters; McGraw Hill (2004); e-books at http://www.mhhe.com/physsci/chemistry/carey5e/Ch20/ch20-3-3-1.html (last visited Feb. 26, 2013).*
Japan Patent Office, Communication dated Apr. 8, 2014, issued in corresponding Japanese application No. 2012-510755.
"Hydrolysis of esters and lactones," Experimental Chemistry Lecture 22, 1999, 4th edition, pp. 6-7.

* cited by examiner

*Primary Examiner* — Fereydoun G Sajjadi
*Assistant Examiner* — Kofi Adzamli
(74) *Attorney, Agent, or Firm* — Sughrue Mion, PLLC

(57) ABSTRACT

The present invention provides a method of preparing an alkylamine derivates which hardly generates impurities and enables mass production with high purity.

18 Claims, No Drawings

PROCESS OF PREPARING AN ALKYLAMINE DERIVATIVE

CROSS REFERENCE TO RELATED APPLICATIONS

This application is a National Stage of International Application No. PCT/KR2010/003057 filed May 14, 2010, claiming priority based on U.S. Provisional Patent Application No. 61/178.117 filed May 14, 2009, the contents of all of which are incorporated herein by reference in their entirety.

FIELD OF INVENTION

The present invention relates to a preparing method enabling mass production of an alkylamine derivative with high purity by using an acid in hydrolysis process of a dialkylamino ester hydrochloride.

BACKGROUND ART

The compound having a $C_4$ framework represented by Chemical Formula 1, of which both of $R_1$ and $R_2$ are methyl group, can be used very usefully for preparing the medicine (HKI-272, Neratinib) represented by Chemical Formula II shown in Scheme 1 and the medicine (BIBW-2992, Tovok) represented by Chemical Formula III shown in Scheme 2.

[Chemical Formula 1]

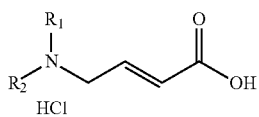

wherein, each of $R_1$ and $R_2$ is independently $C_1$-$C_2$ alkyl group, and preferably methyl group all together.

[Scheme 1]

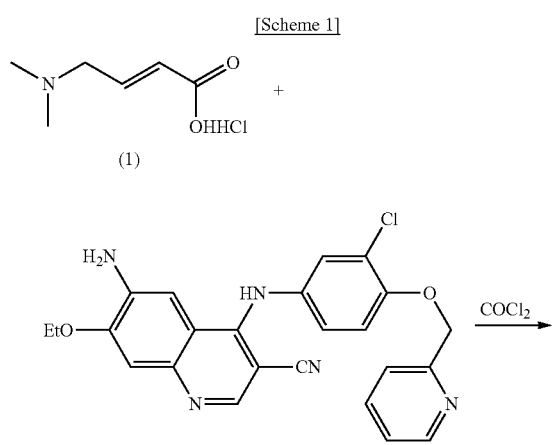

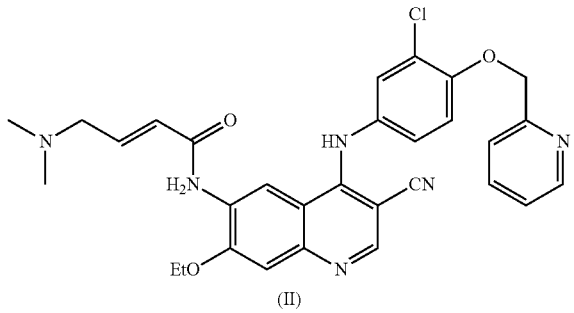

[Scheme 2]

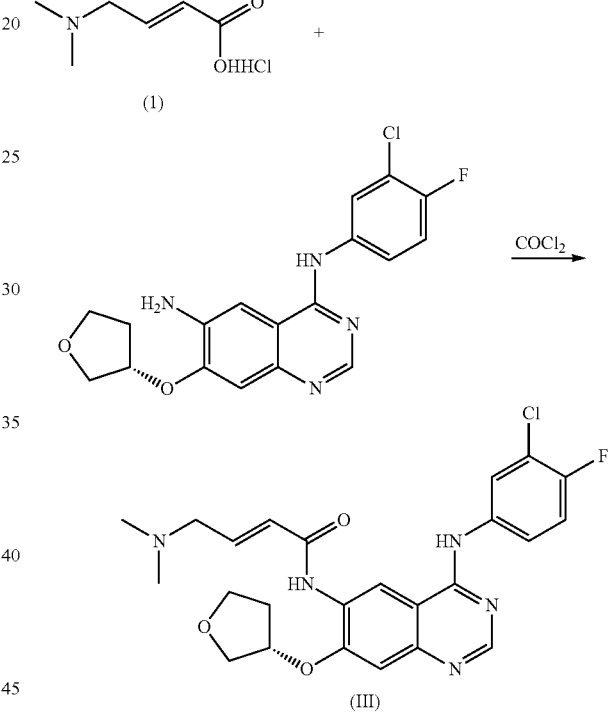

As shown in Scheme 1 and 2, the compound of Chemical Formula 1 is used for preparing the medicines of Chemical Formulae II and III in a form of hydrochloride. The compounds of Chemical Formulae II and III have been used as a HER-2 Tyrosine Kinase Inhibitor, and an anticancer medicine showing a medical activity, and they are known as the compounds having more excellent effect in comparison with side-effect than former other compounds (US 2003/0050222A1, US 2004/0162442 A1, U.S. Pat. No. 7,126,025 B2).

However, the compound of Chemical Formula 1 is scientifically and industrially very interesting and useful compound because there are many limitations for preparing the same. Therefore, a new method for mass-producing the compound of Chemical Formula 1 is needed.

However, there is no technique to mass-produce the compound of Chemical Formula 1 industrially in prior methods except the following Scheme 3 (U.S. Pat. No. 7,126,025, B2).

[Scheme 3]

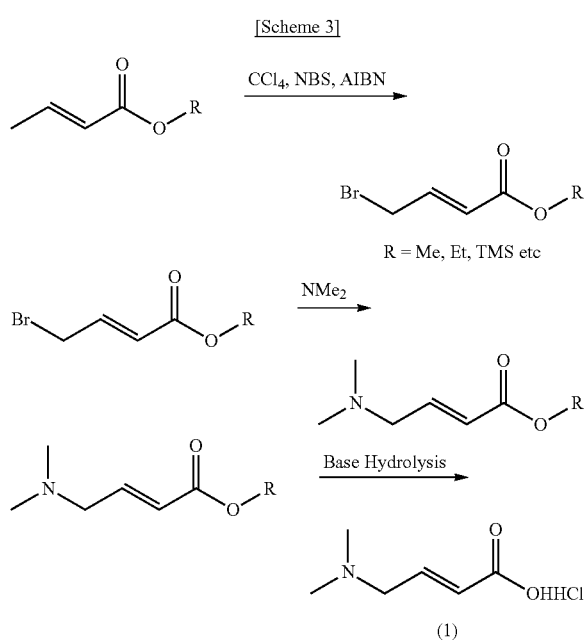

That is, the compound of Chemical Formula 1 is only prepared by the known method of Scheme 3 so far, but there is a problem of using carbon tetrachloride or benzene those are very toxic to human body as a solvent. In addition to, the method has a disadvantage of that intense reaction is inevitable and it has a danger of explosion in the reaction. Therefore, prior method of preparing the compound of Chemical Formula 1 is very restricted due to the problems, and only the methods those are very difficult to be used for industrial mass-production are known.

Furthermore, prior method of preparing the compound of Chemical Formula 1 has fatal problem of that it is inevitable to generate a large quantity of impurity, and thus the compound of Chemical Formula 1 prepared by the method includes a large quantity of impurity. Therefore, if the physiological active materials of Chemical Formulae II and III were prepared by using the compound of Chemical Formula 1 prepared by the method, each of the reactions varies severely in input of raw and subsidiary materials, etc. in the preparing process. In addition to, huge financial costs are needed for purifying the compound after chemical reaction in order to obtain the target compound having a worth as a medicine to be obtained, because it cannot help preparing the compounds of Chemical Formulae II and III including a large quantity of impurity, as a result.

Furthermore, if the compound of Chemical Formula 1 is prepared according to Scheme 3, it is possible to obtain the target compound, but the compound cannot help including many side products, because it is impossible to predict the equivalent needed in the reaction. Physical re-crystallization method and the like are used as a method of eliminating the side products, but the financial cost for eliminating the same becomes excessive, because the structure of the side product is very similar to the compound of Chemical Formula 1. However, the method of preparing or purifying the compound for reducing the impurity below the level needed by the quality basis of medicine is not found yet.

Namely, it is real state that it is impossible to use the compound for preparing the medicine requiring strict impurity level when the compound is prepared by hydrolyzing the ester with the base compound after the bromination and the amination as shown in Scheme 3. Furthermore, it is another fatal disadvantage of the method that it is impossible to obtain the target compound of Chemical Formula 1 with high purity, because large quantity of 4-dimethylamino-3-hydroxybutyric acid (hereinafter, norcarnitine) hydrochloride having a hydroxyl group at position 3 is prepared as impurity and when hydrolyzing the ethyl ester with the base, and the impurity of bis-compound is prepared by introducing the amine group, as shown in Scheme 3.

SUMMARY OF THE INVENTION

The present invention is for resolving the above problems of prior arts, it is an aspect of the present invention to provide a method of preparing an alkylamine derivate inhibiting generation of norcarnitine that is an impurity as much as possible by using an acid in hydrolysis process of a dialkylamino ester hydrochloride.

It is another aspect of the present invention to provide a method of preparing an alkylamine derivate capable of preparing the target compound of Chemical Formula 1 that can be used to medicines of Chemical Formulae II and III with high purity by chemically changing the bis-compound generated during introduction of the amine group into the target compound.

It is still another aspect of the present invention to provide a method of preparing an alkylamine derivate having mild reaction condition, and mass-producible and economical.

In order to attain the object, the present invention provides a method of preparing an alkylamine derivative, including the step of preparing a 4-dialkylamino crotonic acid hydrochloride by hydrolyzing a $C_{1-4}$ alkyl 4-dialkylamino crotonate hydrochloride in the presence of an acid.

The $C_{1-4}$ alkyl 4-dialkylamino crotonate hydrochloride is preferably ethyl 4-dimethylamino crotonate hydrochloride.

Furthermore, the acid used in the hydrolysis is preferably hydrochloric acid, sulfuric acid, benzene sulfonic acid, benzene sulfonic acid substituted by methyl group, carboxylic acid, a $C_{1-3}$ alkyl carboxylic acid, phenyl carboxylic acid, phosphoric acid, bromic acid, or iodic acid.

Furthermore, the 4-dialkylaminocrotonic acid hydrochloride is preferably the compound of Chemical Formula 1:

[Chemical Formula 1]

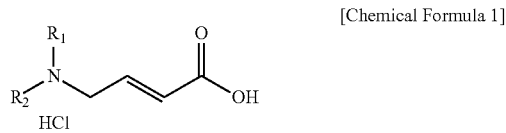

wherein, each of $R_1$ and $R_2$ is independently $C_1$-$C_2$ alkyl group, and preferably methyl group all together.

DETAILED DESCRIPTION OF THE PREFERRED EMBODIMENT

Hereinafter, the present invention is explained in more detail.

The present invention relates to a method of preparing an alkylamine derivate that inhibits generation of impurities during hydrolysis, and can change bis-compound generated during aminating reaction chemically into the target compound. Therefore, the present invention provides a method that is not only industrially useful and easy to mass-produce the compound but also financially effective and possible to produce the 4-dialkylaminocrotonic acid hydrochloride of Chemical Formula 1, the target compound, with mild reaction condition.

Generally, preparation processes of high purity bromide compound and hydrolysis reaction thereof are needed to prepare the compound of Chemical Formula 1. However, it is difficult to prepare the compound of Chemical Formula 1 with high purity in prior methods, because a large quantity of norcarnitine impurity is generated because base compound is used in hydrolysis process and indispensable bis-compound impurity generated in aminating reaction is not eliminated through re-crystallization process.

Namely, by using base compound, such as caustic soda, lithium hydroxide, calcium hydroxide and the like in the hydrolysis process, about 30% or more norcarnitine is generated as the impurity, even though the hydrolysis process is carried out at low temperature. Therefore, the present invention uses an acid catalyst in the hydrolysis process to reduce the impurity, and it is possible to reduce norcarnitine impurity generated in the hydrolysis process to be below 3%. When using the base such as caustic soda, it is impossible to obtain the target compound, the compound of Chemical Formula 1, with high purity of 99% or more, because 3,4-bis(trialkylamino)butyric acid ethyl ester formed during the aminating reaction is changed not into the target compound, the 4-dialkylamino crotonic acid hydrochloride of Chemical Formula 1, but into a 3,4-bis(trialkylamino)butyric acid and the reaction is terminated as it is.

Therefore, the present invention can prepare the alkylamine derivative by including the step of hydrolyzing a $C_{1-4}$ alkyl 4-dialkylamino crotonate hydrochloride in the presence of an acid so as to prepare the 4-dialkylamino crotonic acid hydrochloride, in order to resolve the problems.

According to the method, the reaction of the alkyl 3,4-bis(trialkylamino)butyric acid ethyl ester formed by the aminating reaction is not terminated in the state of the 3,4-bis(trialkylamino)butyric acid. And, the 4-dialkylamino-3-hydroxy butyric acid hydrochloride is 3% or less and the 3,4-bis(trialkylamino)butyric acid dihydrochloride is 0.1% or less in the 4-dialkylamino crotonic acid hydrochloride through the hydrolysis process. Therefore, the present invention can obtain the 4-dialkylaminocrotonic acid hydrochloride with high purity of 99.5% or more and high yield of 70% or more, and it is possible to mass-produce the compound more economically than prior methods.

At this time, the $C_{1-4}$ alkyl 4-dialkylamino crotonate hydrochloride can be prepared by brominating an alkyl 4-hydroxy crotonate so as to prepare a bromide compound, and aminating the same.

Furthermore, the 4-dialkylamino crotonic acid hydrochloride is preferably the compound of Chemical Formula 1:

[Chemical Formula 1]

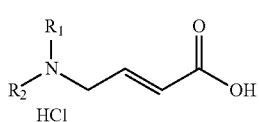

wherein, each of $R_1$ and $R_2$ is independently $C_1$-$C_2$ alkyl group, and preferably methyl group all together.

Hereinafter, the preparing method of the present invention is explained in more detail by referring to the following Scheme 4:

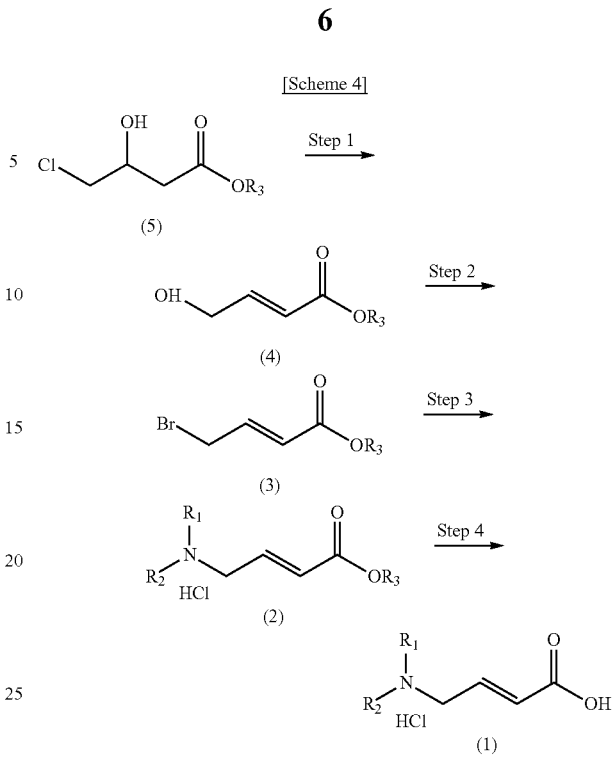

[Scheme 4]

wherein, each of $R_1$ and $R_2$ is independently methyl group or ethyl group, and $R_3$ represents $C_{1-4}$ alkyl group.

As shown in Scheme 4, the present invention can obtain pure alkyl 4-hydroxy crotonate of Chemical Formula 4 by treating the alkyl 4-chloro-3-hydroxy butyrate of Chemical Formula 5 with a caustic soda in anhydrous ethanol (Step 1).

Subsequently, the present invention can obtain pure bromide compound of Chemical Formula 3 by brominating the pure crotonate of Chemical Formula 4 and distillating the same under decompressed condition for purification (Step 2).

The brominating reaction may be carried out under the condition of using triphenyl phosphine bromide. At this time, the triphenyl phosphine bromide, a brominating reagent, may be the compound prepared by reacting triphenyl phosphine with brome or N-bromo succinimide.

Furthermore, an alkyl 4-bromo crotonate may be prepared through brominating reaction including the steps of reacting a $C_1$~$C_8$ alkyl sulfonyl chloride or a $C_0$~$C_1$ substituted benzenesulfonyl chloride with the alkyl 4-hydroxy crotonate so as to prepare a sulfonate compound, and reacting the sulfonate compound with an inorganic bromide such as a metal bromide, or an organic bromide such as a quaternary alkyl ammonium bromide.

At this time, the $C_1$~$C_8$ alkyl sulfonyl chloride is preferably methanesulfonyl chloride. The $C_0$~$C_1$ substituted benzenesulfonyl chloride is preferably benzenesulfonyl chloride or methylbenzene sulfonyl chloride. Furthermore, the metal bromide or the quaternary alkyl ammonium bromide may be sodium bromide, potassium bromide, calcium bromide, lithium bromide, tetramethyl ammonium bromide, tetrabutyl ammonium bromide, or tetraethyl ammonium bromide, and these may be used solely or by mixing two or more compound with the equivalent of 0.1 to 2.

Furthermore, the brominating reaction may be carried out at the low temperature of about 0° C. generally by using an organic solvent that is used in an organic synthesis, such as methylene chloride, THF, DMF and so on.

After the reaction of Step 2, the present invention can prepare the ester hydrochloride compound of Chemical Formula 2 having a dialkylamino group at position 4 by aminating the bromide compound of Chemical Formula 3 (Step 3).

The amination reaction may be carried out by slowly adding a dialkyl amine, preferably dimethyl amine, dissolved in an organic solvent as droplets into the bromide compound of Chemical Formula 3 dissolved in an organic solvent with the equivalent of 2 to 2.5 at low temperature. After the reaction, pure $C_{1-4}$ alkyl 4-dialkylamino crotonate hydrochloride of Chemical Formula 2 can be obtained from the reaction product by using ethyl acetate hydrochloric acid solution.

At this time, the 3,4-bis(trialkylamino)butyric acid ethyl ester compound may be formed in company with the compound of Chemical Formula 2 through the aminating reaction. However, it can be eliminated by subsequent hydrolysis reaction. More specifically, 3,4-bis(trimethylamino)butyric acid ethyl ester may be formed through the reaction by dimethyl amine.

At this time, common alkyl acetate hydrochloric acid solution such as methyl acetate hydrochloric acid solution and the like as well as ethyl acetate hydrochloric acid solution may be used for preparing the hydrochloride compound.

Furthermore, any organic solvent that is used for common organic synthesis, such as methylene chloride, THF, DMF and so on, can be used in the present invention, and the kind of the solvent is not limited particularly. Furthermore, the aminating reaction is preferably carried out at the temperature of −10° C. to 10° C.

After the reaction of Step 3, the present invention can provide the 4-dialkylamino crotonic acid hydrochloride of Chemical Formula 1 by hydrolyzing the alkyl 4-dialkylamino crotonate hydrochloride of Chemical Formula 2 with an acid. Particularly, the present invention can minimize the content of impurity because the norcarnitine is reduced to 3% or less by using an acid in the hydrolysis reaction. Furthermore, the present invention is characterized in that the 3,4-bis(trialkylamino) butyrate is changed into the 4-dialkylamino crotonic acid of Chemical Formula 1, the target compound, by hydrolyzing the ester group of the compound of Chemical Formula 2 by using an acid catalyst or an acid.

According to the present invention, 4-dimethylamino-3-hydroxybutyric acid hydrochloride (that is, norcarnitine) of 10% or less is formed as the impurity through the hydrolysis reaction. Furthermore, since the 3,4-bis(trialkylamino)butyric acid dihydrochloride is eliminated through the hydrolysis reaction, the content of 4-dimethylamino-3-hydroxybutyric acid hydrochloride formed as the impurity is limited to 3% or less. Therefore, the 3,4-bis(trialkylamino)butyric acid dihydrochloride of 0.1% or less is left as the impurity. And, barely 4-dimethylamino-3-hydroxybutyric acid hydrochloride of 3% or less may be formed. Furthermore, the 3,4-bis(trialkylamino)butyric acid dihydrochloride is eliminated by re-crystallization after the hydrolysis reaction. Therefore, it is possible to reduce the content of 4-dimethylamino-3-hydroxybutyric acid hydrochloride to be 0.1% or less and to produce the 4-dialkylamino crotonic acid hydrochloride including the 3,4-bis(trialkylamino)butyric acid dihydrochloride of 0.02% or less. According to this, the present invention can provide pure 4-dialkylamino crotonic acid hydrochloride, the target compound, with high purity of 99.5% or more.

At this time, the hydrolysis reaction may be carried out by using water and a little amount of acid catalyst, and pure 4-dialkylamino crotonic acid hydrochloride can be obtained with a purity of 99.5% or more and a yield of 70% or more by carrying out the crystallization in isopropanol after the hydrolysis reaction.

Furthermore, the acid used in the hydrolysis is preferably hydrochloric acid, sulfuric acid, benzene sulfonic acid, benzene sulfonic acid substituted by methyl group, carboxylic acid, a $C_{1-3}$ alkyl carboxylic acid, phenyl carboxylic acid, phosphoric acid, bromic acid, or iodic acid. More preferably, hydrochloric acid is used because it does not require the additional process for eliminating the acid catalyst.

The acid is preferably used in the equivalent of 1.05 to 10, preferably in the equivalent of 1.1 to 1.2 per the $C_{1-4}$ alkyl 4-dialkylamino crotonate hydrochloride. At this time, when the hydrolysis is carried out with the content beyond the above range, excess norcarnitine is formed and it is impossible to reduce economically the impurity to be 0.1% or less in the crystallization step.

Furthermore, the hydrolysis may be carried out at the temperature of 50 to 110° C., and preferably of 90 to 105° C. When the temperature of the hydrolysis is under 50° C., the elimination reaction of the bis-compound impurity does not occur during the hydrolysis of the ester. Furthermore, it is economically not preferable to elevate the temperature over 110° C. because it requires excess heat energy. Furthermore, the temperature is preferably to be 90 to 105° C., because the processing time for changing the bis-compound impurity to the target compound and the reaction speed for producing norcarnitine are rapid and there is a possibility of forming norcarnitine to be 3% or more during the hydrolysis reaction.

In the present invention, the method includes the steps of reacting ethyl 4-dimethylamino crotonate in an aqueous solution of 90 to 105° C. by using hydrochloric acid catalyst, and re-crystallizing the same so as to prepare the 4-dialkylamino crotonic acid hydrochloride wherein the 4-dimethylamino-3-hydroxy butyric acid hydrochloride and 3,4-bis trimethylamino butyric acid dihydrochloride is left 0.02% or less.

When the compound of Chemical Formula 1 prepared according to the above method is used to prepare medicines (HKI-272, BIBW-2992 and the like), the purifying process can be minimized because the compound has almost no impurity.

[Best Mode]

Hereinafter, the present invention provides preferable examples for the understanding of the present invention. However, the following examples are only for explaining the present invention and the present invention is not limited to or by them.

Example 1

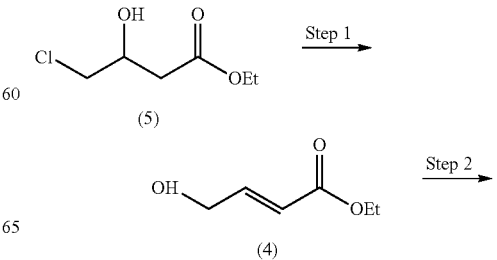

[Scheme 4-1]

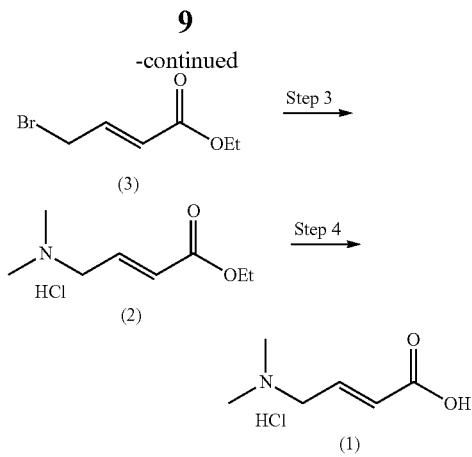

Step 1

After introducing ethyl 4-chloro-3-hydroxy butyrate (200 g, 1.2 mol) and anhydrous EtOH (1200 mL) into a 3 L one-neck flask, a solution that NaOH (52.8 g, 1.1 eq) is completely dissolved in anhydrous EtOH (800 mL) was slowly added therein at 0° C. After all of NaOH solution was added, the temperature was naturally elevated to room temperature and the solution was stirred for about 15 hours. When the reaction is finished, AcOH (69 mL, 1 eq) was added therein and the solution was stirred for 10 minutes, and then EtOH was eliminated by concentrating the same.

After extracting organic materials from the concentrated solution by adding methylene chloride (1 L) and water (1 L) therein, the organic material was extracted from the water layer with methylene chloride (1 L) twice. The collected organic layer was washed with NaHCO$_3$ (600 mL) and dried with anhydrous MgSO$_4$, and then (E)-ethyl 4-hydroxybut-2-enoate of 133 g was obtained with a yield of 85% by filtering and concentrating the same.

$^1$H-NMR (δ ppm, CDCl$_3$, 400 Mz): 6.95 (m, 1H), 6.00 (m, 1H), 4.25 (m, 2H), 4.10 (q, 2H), 1.20 (t, 3H)

Step 2

Triphenyl phosphine (295 g, 1.12 mol) and methylene chloride (665 mL) were introduced into a 3 L one-neck flask and were stirred for 10 minutes at 0° C. And then, bromine (179.3 g) dissolved in methylene chloride (665 mL) was slowly added as droplets therein for 1 hours. At this time, the temperature of the reactor was maintained to be 0° C. The reaction product was further stirred for 30 minutes after all of bromine was added. (E)-ethyl 4-hydroxybut-2-enoate (133 g, 1.02 mol) dissolved in methylene chloride (665 mL) was slowly added as droplets into the reaction mixture for 1 hours. At this time, the temperature of the reactor was also maintained to be 0° C. After all of (E)-ethyl 4-hydroxybut-2-enoate was added, the mixture was further stirred for 30 minutes at 0° C. (the reaction was confirmed with TLC, EtOAc:hexane=1:4). After washing the organic layer of the reaction product with water (900 mL×2), the organic layer was dried with anhydrous MgSO$_4$, and then a large quantity of Ph$_3$P=O was extracted in company with the product by filtering and concentrating the same. The triphenyl phosphine oxide was eliminated by filtering the product, after adding n-hexane (1 L) therein and stirring the same for 30 minutes with a mechanical stirrer. (E)-ethyl 4-bromobut-2-enoate of 160 g was obtained with a yield of 81.2% by concentrating the filtered solution under a decompressed condition and distillating the concentrated solution under vacuum condition.

$^1$H-NMR (δppm, CDCl$_3$, 400 Mz): 6.92 (m, 1H), 5.95 (m, 1H), 4.15 (q, 2H), 3.95 (m, 2H), 1.25 (t, 3H)

Step 3

(E)-ethyl 4-bromobut-2-enoate (160 g, 0.83 mol) and methylene chloride (1.6 L) were introduced into 5 L three-neck flask and stirred for 10 minutes at −10° C. 50% Me$_2$NH (187.1 g, 2.5 eq) was extracted by methylene chloride (1.6 L), and water layer was drained. And then, a solution that Me$_2$NH was dissolved in methylene chloride was slowly added as droplets into the flask for 1 hour. At this time, the internal temperature of the reactor was maintained to be 5° C. or less. After all of Me$_2$NH solution dissolved in methylene chloride was added, the degree of the reaction was confirmed with TLC, and the mixture was stirred until the starting materials were not seen. At this time, the stirring required about 30 minutes and it was needed to pay attention that the reaction time did not get long. Water (1280 mL) was added to the reaction solution. The reaction mixture was separated by using a separating funnel, and then the organic layer was washed with an aqueous base solution in which NaOH (66.4 g, 2 eq) dissolved in water (830 mL) and brine solution (800 mL) were mixed. The separated organic layer was dried with anhydrous MgSO$_4$, and then filtered and concentrated. After transferring the concentrated solution into 2 L two-neck flask and dissolving the same in EtOAc (1380 mL), EtOAc solution (222 mL, 1.2 eq) in which 4.5 M HCl was dissolved was slowly added as droplets therein. After the temperature of the reacting flask fell down to room temperature, the reaction mixture was filtered with a filter and the solid left in the filter was washed with EtOAc (500 mL). The solid was transferred into one-neck flask and dried with a decompression device, and then (E)-ethyl 4-(dimethylamino)but-2-enoate hydrochloride of 128.6 g was obtained with a yield of 80%.

$^1$H-NMR (δppm, D$_2$O, 400 Mz): 6.85 (m, 1H), 6.23 (m, 1H), 4.15 (q, 2H), 4.90 (d, 2H), 2.85 (s, 6H), 1.25 (t, 3H)

Step 4

(E)-ethyl 4-(dimethylamino)but-2-enoate hydrochloride (20 g, 0.103 mol) was dissolved in water (102 mL) in 250 mL two-neck flask, and then conc. HCl (2.6 mL) was added therein. After refluxing the reaction mixture for 3 hours, the temperature of the reaction mixture was reduced to room temperature. EtOH formed in the reaction was eliminated by distillation under reduced pressure, and then water (34 mL) was added therein. After adding conc. HCl (1.3 mL) therein again, the reaction mixture was refluxed again for 2 hours and water in the reaction mixture was eliminated by distillation under reduced pressure. Re-crystallization was carried out by adding IPA (100 mL) to the solid remained therein. At this time, IPA solution was heated to the temperature of 40 to 50° C., and the solution was stirred for 2 hours at room temperature. After filtering the solid with a filter, the solid was washed with IPA (10 mL). (E)-4-(dimethylamino) but-2-enoic acid hydrochloride of 12 g was obtained with a yield of 70% by drying the collected solid (99.8% Purity by HPLC, Corona Detector).

$^1$H-NMR (δppm, D$_2$O, 400 Mz): 6.95 (m, 1H), 6.30 (m, 1H), 4.00 (m, 2H), 2.9d (s, 6H)

Comparative Example

Steps 1 to 3 were carried out according to the same as the Example, and Step 4 was carried out as follows instead of Step 4 of the Example.

That is, after dissolving (E)-ethyl 4-(dimethylamino)but-2-enoate hydrochloride of 16 g in water (100 mL), 50% aqueous caustic soda solution of 16 g were slowly added as droplets therein for 1 hour at 5° C. or less, and the hydrolysis was carried out for 2 hours at the same temperature. After adjusting the pH of the reaction solution to 7 by using hydrochloric acid, the aqueous solution was eliminated and the ratio of formed norcarnitine was confirmed with NMR. Furthermore, another reaction was carried out according to the same as above conditions except that the temperature was −20° C. or less. The pH was adjusted to 7 and the aqueous solution was eliminated, and the ratio of formed norcarnitine was confirmed with NMR. Both reactions at different temperature were carried out by using lithium hydroxide and calcium hydroxide commonly, and analyzed.

Norcarnitine: $^{1}$H-NMR (D$_2$O, δppm, 400 Mz): 4.35 (m, 1H), 3.20 (m, 2H), 2.91 (s, 6H), 2.45 (d, 2H)

Bis-compound impurity: $^{1}$H-NMR (D$_2$O, δppm, 400 Mz): 4.25 (m, 1H), 3.71 (m, 2H), 3.15 (m, 2H), 3.09 (s, 6H), 2.96 (s, 2H)

As a result of NMR analysis, it can be identified that all of 6 reactions using base compound show that norcarnitine having above NMR pattern was formed 30% or more per the target compound. Furthermore, the bis-compound impurity that was formed in an amount of 5% or less in Step 3 shows a NMR pattern of that only ethylester was hydrolyzed. It means that a large quantity of norcarnitine was formed and the bis-compound impurity could not be removed when the base compound was used.

What is claimed is:

1. A process for preparing a dialkylamino crotonic acid hydrochloride of Chemical Formula 1, comprising the step of
    brominating a C$_{1-4}$ alkyl 4-hydroxy crotonate so as to make a bromide compound,
    aminating the bromide compound to prepare a C$_{1-4}$ alkyl 4-dialkylamino crotonate hydrochloride,
    hydrolyzing the C$_{1-4}$ alkyl 4-dialkylamino crotonate hydrochloride in the presence of an acid,
    wherein the hydrolysis is carried out at a temperature of 50 to 110 ° C.

Chemical Formula 1

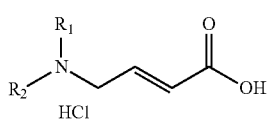

wherein, each of R$_1$ and R$_2$ is independently C$_1$-C$_2$ alkyl group.

2. The process of claim 1, wherein the C$_{1-4}$ alkyl 4-dialkylamino crotonate hydrochloride is ethyl 4-dimethylamino crotonate hydrochloride.

3. The process of claim 1, wherein the acid is hydrochloric acid, sulfuric acid, benzene sulfonic acid, benzene sulfonic acid substituted by methyl group, carboxylic acid, a C$_{1-3}$ alkyl carboxylic acid, phenyl carboxylic acid, phosphoric acid, bromic acid, or iodic acid.

4. The process of claim 3, wherein the acid is hydrochloric acid.

5. The process of claim 4, wherein 1.05 to 10 equivalents of the acid is used per the C$_{1-4}$ alkyl 4-dialkylamino crotonate hydrochloride.

6. The process of claim 5, wherein 1.1 to 1.2 equivalents of the acid is used per the 4-dialkylamino crotonate hydrochloride.

7. The process of claim 1, wherein 3,4-bis(trimethylamino) butyric acid dihydrochloride of 0.1% or less is left after the hydrolysis.

8. The process of claim 1, wherein the method forms 4-dimethylamino-3- hydroxybutric acid hydrochloride of 10% or less as impurities through the hydrolysis.

9. The process of claim 8, wherein the method forms 4-dimethylamino-3-hydroxybutric acid hydrochloride of 3% or less as impurities through the hydrolysis.

10. The process of claim 8, wherein the method leaves 4-dimethylamino-3-hydroxybutyric acid hydrochloride of 0.1% or less as impurities through re-crystallization after the hydrolysis.

11. The process of claim 1, wherein the method prepares the 4-dialkylamino crotonic acid hydrochloride with a purity of 99.5% or more.

12. The process of claim 1, wherein the brominating reaction is carried out by using triphenyl phosphine bromide.

13. The process of claim 12, wherein the triphenyl phosphine bromide is prepared by reacting triphenyl phosphine with bromine or bromo succinimide.

14. The process of claim 1, wherein an alkyl 4-bromo crotonate is prepared through brominating reaction including the steps of reacting a C$_1$~C$_8$ alkyl sulfonyl chloride or a C$_0$~C$_1$ substituted benzenesulfonyl chloride with an alkyl 4-hydroxyy crotonate so as to prepare a sulfonate compound, and reacting the sulfonate compound with a metal bromide or a quaternary alkyl ammonium bromide.

15. The process of claim 14, wherein the C$_1$~C$_8$ alkyl sulfonyl chloride is methanesulfonyl chloride.

16. The process of claim 14, wherein the metal bromide or the quaternary alkyl ammonium bromide is one or more selected from the group consisting of sodium bromide, potassium bomide, calcium bromide, lithium bromide, tetramethyl ammonium bromide, tetrabutyl ammonium bromide, and tetraethyl ammonium bromide; and
    wherein the metal bromide or the quaternary alkyl ammonium bromide is used in an amount of 0.1 to 2 equivalents per the sulfonate compound.

17. The process of claim 1, wherein the C$_{1-4}$ alkyl 4-dialkylamino crotonate hydrochloride is ethyl 4-dimethylamino crotonate and the acid is hydrochloric acid; and
    wherein the hydrolysis of the C$_{1-4}$ alkyl 4-dialkylamino crotonate hydrochloride is carried out at a temperature of 90 to 105 ° C.

18. The process of claim 17, further comprising recrystallizing the hydrolysis product, wherein the recrystallization product contains 0.02% or less of 4-dimethylamino-3-hydroxybutyric acid hydrochloride and 3,4-bis(trimethylamino)butyric acid dihydrochloride.

* * * * *